(12) United States Patent
Hahn et al.

(10) Patent No.: US 9,056,264 B2
(45) Date of Patent: Jun. 16, 2015

(54) BIOCOMPATIBLE TUBING FOR LIQUID CHROMATOGRAPHY SYSTEMS

(75) Inventors: Mark Hahn, Oak Harbor, WA (US); Scott J. Ellis, Anacortes, WA (US); Eric Beemer, Anacortes, WA (US)

(73) Assignee: IDEX Health & Science LLC, Oak Harbor, WA (US)

( * ) Notice: Subject to any disclaimer, the term of this patent is extended or adjusted under 35 U.S.C. 154(b) by 492 days.

(21) Appl. No.: 13/206,873

(22) Filed: Aug. 10, 2011

(65) Prior Publication Data

US 2012/0024411 A1    Feb. 2, 2012

Related U.S. Application Data

(63) Continuation-in-part of application No. 12/838,032, filed on Jul. 16, 2010, now Pat. No. 8,569,070.

(60) Provisional application No. 61/372,427, filed on Aug. 10, 2010, provisional application No. 61/474,653, filed on Apr. 12, 2011.

(51) Int. Cl.
*G01N 30/02* (2006.01)
*F16L 58/10* (2006.01)
*B01D 15/22* (2006.01)
*F16L 9/14* (2006.01)
*G01N 30/60* (2006.01)

(52) U.S. Cl.
CPC ........... *B01D 15/22* (2013.01); *Y10T 29/49826* (2015.01); *F16L 9/14* (2013.01); *F16L 58/10* (2013.01); *G01N 30/6004* (2013.01); *G01N 30/6039* (2013.01); *G01N 30/6073* (2013.01)

(58) Field of Classification Search
CPC ..... G01N 30/02; F16L 58/10; F16L 58/1018; F16L 58/1054; F16L 9/14; F16L 9/147; F16L 11/005
USPC ........... 422/70, 89; 436/161; 73/23.35–23.42, 73/61.52–61.59; 210/198.2, 656; 95/82–89; 96/101–107
See application file for complete search history.

(56) References Cited

U.S. PATENT DOCUMENTS

| | | |
|---|---|---|
| 3,904,527 A | 9/1975 | Wilhelmson et al. |
| 5,472,598 A | 12/1995 | Schick |
| 5,482,628 A | 1/1996 | Schick |
| 5,525,303 A | 6/1996 | Ford et al. |
| 5,651,885 A | 7/1997 | Schick |
| 5,730,943 A | 3/1998 | Ford et al. |
| 5,736,036 A * | 4/1998 | Upchurch et al. ......... 210/198.2 |

(Continued)

FOREIGN PATENT DOCUMENTS

| | | |
|---|---|---|
| EP | 0624795 A2 | 11/1994 |
| EP | 1452864 A1 | 9/2004 |

(Continued)

OTHER PUBLICATIONS

Machine translation JP 2008-051689, downloaded Nov. 16, 2013.*

(Continued)

*Primary Examiner* — Jan Ludlow
(74) *Attorney, Agent, or Firm* — Vinson & Elkins LLP

(57) ABSTRACT

A biocompatible tube that can be used in a liquid chromatography system is described. The tube can have flanged or straight ends, and can be used in conjunction with one or more fitting, assembly.

15 Claims, 7 Drawing Sheets

(56) References Cited

U.S. PATENT DOCUMENTS

| | | | |
|---|---|---|---|
| 5,840,953 A * | 11/1998 | Potts | 556/483 |
| 5,938,919 A | 8/1999 | Najafabadi | |
| 6,095,572 A | 8/2000 | Ford et al. | |
| 7,311,502 B2 | 12/2007 | Gerhardt et al. | |
| 8,569,070 B2 * | 10/2013 | Ellis et al. | 436/161 |
| 2005/0269264 A1 | 12/2005 | Fermier et al. | |
| 2007/0283746 A1 | 12/2007 | Gerhardt et al. | |
| 2011/0000279 A1 * | 1/2011 | Miyazaki et al. | 73/23.35 |

FOREIGN PATENT DOCUMENTS

| | | |
|---|---|---|
| EP | 1457775 B1 | 9/2004 |
| GB | 2238257 A | 5/1991 |
| JP | 2008 051689 A | 3/2008 |
| WO | WO 2005/015162 A2 | 2/2005 |
| WO | WO 2005/015162 A3 | 2/2005 |
| WO | WO 2009/088663 A1 | 7/2009 |
| WO | WO 2011/076244 A1 | 6/2011 |

OTHER PUBLICATIONS

International Search Report and Written Opinion of the International Searching Authority, International Patent Application No. PCT/US2011/047218, Dec. 30, 2011.

* cited by examiner

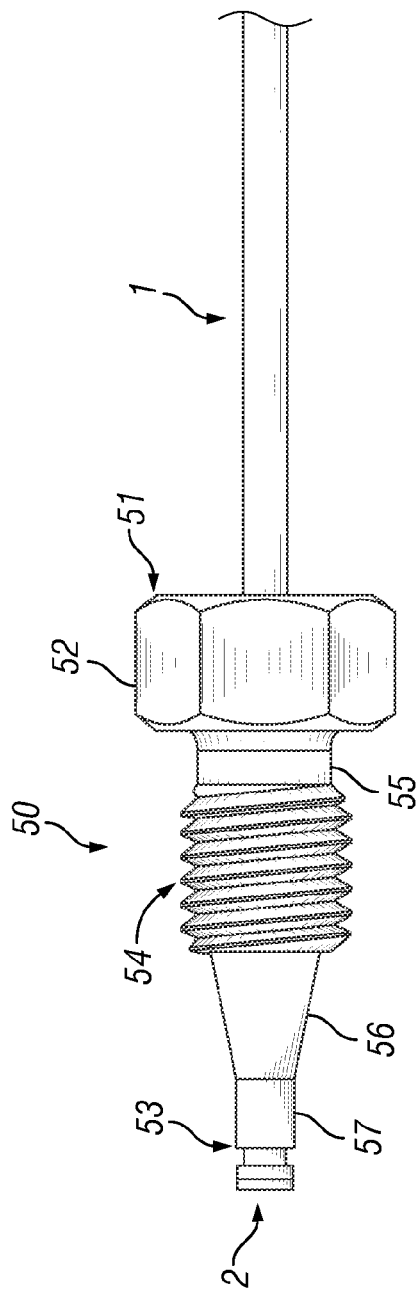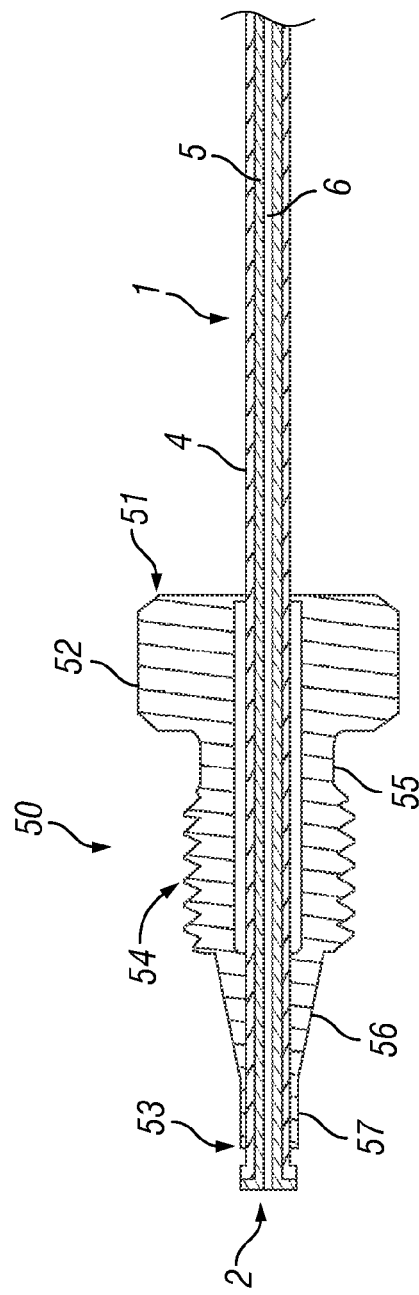
FIG. 6
FIG. 7

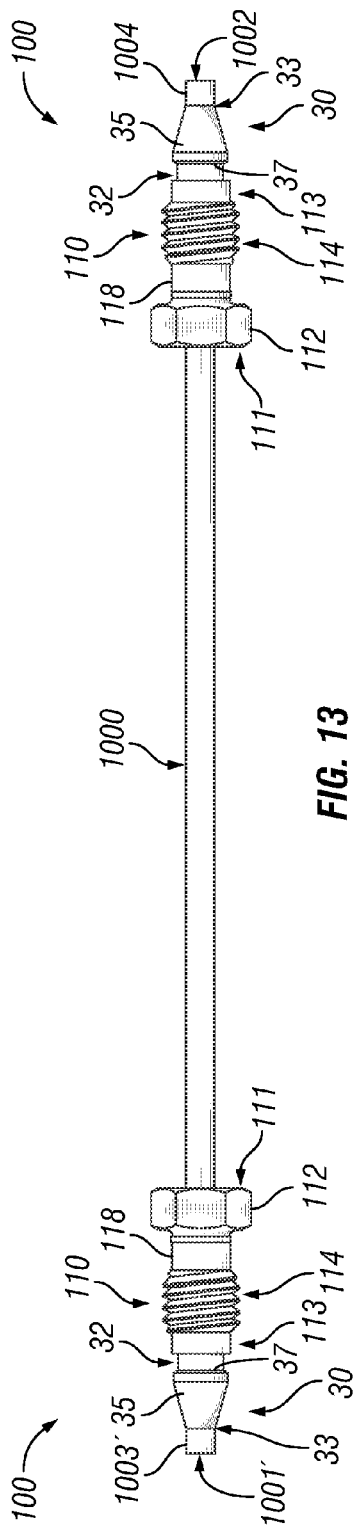
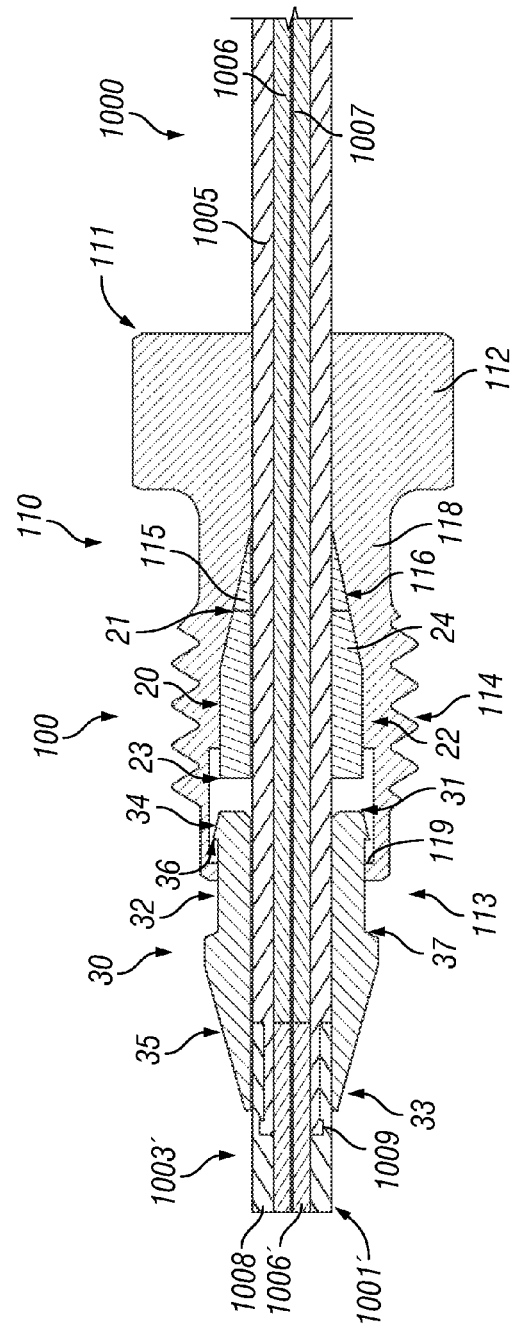
FIG. 13
FIG. 14

BIOCOMPATIBLE TUBING FOR LIQUID CHROMATOGRAPHY SYSTEMS

CROSS-REFERENCE FOR RELATED APPLICATION

This application claims the benefit of U.S. Provisional Patent Application Ser. No. 61/372.427, filed Aug. 10, 2010, and U.S. Provisional Patent Application Ser. No. 61/474,653, filed Apr. 12, 2011, and is a continuation-in-part of U.S. patent application Ser. No. 12/838,032, filed Jul. 16, 2010, each of which are incorporated herein by reference in their entirety.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of the Invention

This invention relates generally to tubing for use in connecting components of liquid chromatography and other analytical systems, and relates more particularly to tubing that is coated or lined with a biocompatible polymer for use in connecting components in liquid chromatography systems used in ultra-high pressure liquid chromatography.

2. Description of the Related Art

Liquid chromatography (LC) is a well-known technique for separating the constituent elements in a given sample. In a conventional LC system, a liquid solvent (referred to as the "mobile phase") is introduced from a reservoir and is pumped through the LC system. The mobile phase exits the pump under pressure. The mobile phase then travels via tubing to a sample injection valve. As the name suggests, the sample injection valve allows an operator to inject a sample into the LC system, where the sample will be carried along with the mobile phase.

In a conventional LC system, the sample and mobile phase pass through one or more filters and often a guard column before coming to the column. A typical column usually consists of a piece of steel tubing which has been packed with a "packing" material. The "packing" consists of the particulate material "packed" inside the column. It usually consists of silica- or polymer-based particles, which are often chemically bonded with a chemical functionality. The packing material is also known as the stationary phase. One of the fundamental principles of separation is the mobile phase continuously passing through the stationary phase. When the sample is carried through the column (along with the mobile phase), the various components (solutes) in the sample migrate through the packing within the column at different rates (i.e., there is differential migration of the solutes). In other words, the various components in a sample will move through the column at different rates. Because of the different rates of movement, the components gradually separate as they move through the column. Differential migration is affected by factors such as the composition of the mobile phase, the composition of the stationary phase (i.e., the material with which the column is "packed"), and the temperature at which the separation takes place. Thus, such factors will influence the separation of the sample's various components.

Once the sample (with its components now separated) leaves the column, it flows with the mobile phase past a detector. The detector detects the presence of specific molecules or compounds. Two general types of detectors are used in LC applications. One type measures a change in some overall physical property of the mobile phase and the sample (such as their refractive index). The other type measures only some property of the sample (such as the absorption of ultraviolet radiation). In essence, a typical detector in a LC system can measure and provide an output in terms of mass per unit of volume (such as grams per milliliter) or mass per unit of time (such as grams per second) of the sample's components. From such an output signal, a "chromatogram" can be provided; the chromatogram can then be used by an operator to determine the chemical components present in the sample.

In addition to the above components, a LC system will often include filters, check valves, a guard column, or the like in order to prevent contamination of the sample or damage to the LC system. For example, an inlet solvent filter may be used to filter out particles from the solvent (or mobile phase) before it reaches the pump. A guard column is often placed before the analytical or preparative column; i.e., the primary column. The purpose of such a guard column is to "guard" the primary column by absorbing unwanted sample components that might otherwise bind irreversibly to the analytical or preparative column.

In practice, various components in an LC system may be connected by an operator to perform a given task. For example, an operator will select an appropriate mobile phase and column, then connect a supply of the selected mobile phase and a selected column to the LC system before operation. In order to be suitable for high performance liquid chromatography (HPLC) applications, each connection must be able to withstand the typical operating pressures of the HPLC system. If the connection is too weak, it may leak. Because the types of solvents that are sometimes used as the mobile phase are often toxic and because it is often expensive to obtain and/or prepare many samples for use, any such connection failure is a serious concern.

It is fairly common for an operator to disconnect a column (or other component) from a LC system and then connect a different column (or other component) in its place after one test has finished and before the next begins. Given the importance of leak-proof connections, especially in HPLC applications, the operator must take time to be sure the connection is sufficient. Replacing a column (or other component) may occur several times in a day. Moreover, the time involved in disconnecting and then connecting a column (or other component) is unproductive because the LC system is not in use and the operator is engaged in plumbing the system instead of preparing samples or other more productive activities. Hence, the replacement of a column in a conventional LC system involves a great deal of wasted time and inefficiencies.

Given concerns about the need for leak-free connections, conventional connections have been made with stainless steel tubing and stainless steel end fittings. More recently, however, it has been realized that the use of stainless steel components in a LC system have potential drawbacks in situations involving biological samples. For example, the components in a sample may attach themselves to the wall of stainless steel tubing. This presents problems because the detector's measurements (and thus the chromatogram) of a given sample may not accurately reflect the sample if some of the sample's components or ions remain in the tubing, and do not pass the detector. Perhaps of even greater concern, however, is the fact that ions from the stainless steel tubing may detach from the tubing and flow past the detector, thus leading to potentially erroneous results. Additionally, ions can easily bind to biological compounds of interest, resulting in changes to the molecules that affect their retention time in the column. Hence, there is a need for "biocompatible" connections through the use of a material that is chemically inert with respect to such "biological" samples and the mobile phase used with such samples so that ions will not be released by the tubing and thus contaminate the sample.

In many applications using selector/injector valves to direct fluid flows, and in particular in liquid and gas chromatography, the volume of fluids is small. This is particularly true when liquid or gas chromatography is being used as an analytical method as opposed to a preparative method. Such methods often use capillary columns and are generally referred to as capillary chromatography. In capillary chromatography, both gas phase and liquid phase, it is often desired to minimize the internal volume of the selector or injector valve. One reason for this is that a valve having a large volume will contain a relatively large volume of liquid, and when a sample is injected into the valve the sample will be diluted, decreasing the resolution and sensitivity of the analytical method.

Micro-fluidic analytical processes also involve small sample sizes. As used herein, sample volumes considered to involve micro-fluidic techniques can range from as low as volumes of only several picoliters or so, up to volumes of several milliliters or so, whereas more traditional LC techniques, for example, historically often involved samples of about one microliter to about 100 milliliters in volume. Thus, the micro-fluidic techniques described herein involve volumes one or more orders of magnitude smaller in size than traditional LC techniques. Micro-fluidic techniques can also be expressed as those involving fluid flow rates of about 0.5 ml/minute or less.

Most conventional HPLC systems include pumps which can generate relatively high pressures of up to around 5,000 psi to 6,000 psi or so. In many situations, an operator can obtain successful results by operating a LC system at "low" pressures of anywhere from just a few psi or so up to 1,000 psi or so. More often than not, however, an operator will find it desirable to operate a LC system at relatively "higher" pressures of over 1,000 psi.

Another, relatively newer liquid chromatography form is Ultra High Performance Liquid Chromatography (UHPLC) in which system pressure extends upward to about 1400 bar or 20,000 psi or so, or even more. In order to achieve greater chromatographic resolution and higher sample throughput, the particle size of the stationary phase has become extremely small. A stationary phase particle as small as 1 micron is common; the resulting high column packing density leads to substantially increased system pressure at the head of the column. Both HPLC and UHPLC are examples of analytical instrumentation that utilize fluid transfer at elevated pressures. For example, in U.S. Patent Publication No. US 2007/0283746 A1, published on Dec. 13, 2007 and titled "Sample Injector System for Liquid Chromatography," an injection system is described for use with UHPLC applications, which are said to involve pressures in the range from 20,000 psi to 120,000 psi. In U.S. Pat. No. 7,311,502, issued on Dec. 25, 2007 to Gerhardt, et al., and titled "Method for Using a Hydraulic Amplifier Pump in Ultrahigh Pressure Liquid Chromatography," the use of a hydraulic amplifier is described for use in UHPLC systems involving pressures in excess of 25,000 psi. In U.S. Patent Publication No. US 2005/0269264 A1, published on Dec. 8, 2005 and titled "Chromatography System with Gradient Storage and Method for Operating the Same," a system for performing UHPLC is disclosed, with UHPLC described as involving pressures above 5,000 psi (and up to 60,000 psi). Applicants hereby incorporate by reference as if fully set forth herein U.S. Pat. No. 7,311,502 and US Patent Publications Nos. US 2007/0283746 A1 and US 2005/0269264 A1.

As noted, liquid chromatography (as well as other analytical) systems, including HPLC or UHPLC systems, typically include several components. For example, such a system may include a pump; an injection valve or autosampler for injecting the analyte; a precolumn filter to remove particulate matter in the analyte solution that might clog the column; a packed bed to retain irreversibly adsorbed chemical material; the HPLC column itself; and a detector that analyzes the carrier fluid as it leaves the column. These various components may typically be connected by a miniature fluid conduit, or tubing, such as metallic or polymeric tubing, usually having an internal diameter of 0.001 to 0.040 inch.

All of these various components and lengths of tubing are typically interconnected by threaded fittings. Fittings for connecting various LC system components and lengths of tubing are disclosed in prior patents, for example, U.S. Pat. Nos. 5,525,303; 5,730,943; and 6,095,572, the disclosures of which are herein all incorporated by reference as if fully set forth herein. Often, a first internally threaded fitting seals to a first component with a ferrule or similar sealing device. The first fitting is threadedly connected through multiple turns by hand or by use of a wrench or wrenches to a second fitting having a corresponding external fitting, which is in turn sealed to a second component by a ferrule or other seal. Disconnecting these fittings for component replacement, maintenance, or reconfiguration often requires the use of a wrench or wrenches to unthread the fittings. Although a wrench or wrenches may be used, other tools such as pliers or other gripping and holding tools are sometimes used. It will be understood by those skilled in the art that, as used herein, the term "LC system" is intended in its broad sense to include all apparatus and components in a system used in connection with liquid chromatography, whether made of only a few simple components or made of numerous, sophisticated components which are computer controlled or the like. Those skilled in the art will also appreciate that an LC system is one type of an analytical instrument (AI) system. For example, gas chromatography is similar in many respects to liquid chromatography, but obviously involves a gas sample to be analyzed. Such analytical instrument systems include high performance or high pressure liquid chromatography systems, an ultra high performance or ultra high pressure liquid chromatography system, a mass spectrometry system, a microflow chromatography system, a nanoflow chromatography system, a nano-scale chromatography system, a capillary electrophoresis system, a reverse-phase gradient chromatography system, or a combination thereof. Although the following discussion focuses on liquid chromatography, those skilled in the art will appreciate that much of what is said also has application to other types of AI systems and methods.

Increasing pressure requirements in liquid chromatography have necessitated the use of high pressure fluidic components. For many applications regular stainless steel tubing can be used to withstand the high pressure. However, for some types of analyses (e.g., biological testing and metal/ion analysis), stainless steel or other metals are not desired in the fluid path as the metal could interfere with the testing. Additionally, there are some fields of use (e.g., nano-scale or nano-volume analysis), that require very small inside diameters to accommodate the extremely low volumes required by these applications. Such small inside diameters are typically not available in stainless steel or other high pressure tubing.

Therefore, it is an object of the present invention to provide biocompatible tubing for use in an HPLC or UHPLC system. An additional object of the present invention is to provide biocompatible tubing with very small inside diameters that can be used in nano-scale or nano-volume applications.

The above and other advantages of the present invention will become readily apparent to those skilled in the art from the following detailed description of the present invention, and from the attached drawings, which are briefly described below.

SUMMARY OF THE INVENTION

In a first embodiment of the present disclosure, a tube is provided that is well-suited for use in liquid chromatography systems, and is particularly well-suited for use in high pressure liquid chromatography and ultra high pressure liquid chromatography, and methods such as in vitro diagnostics (IVD). In this embodiment, the tube comprises an outer layer and an inner biocompatible layer defining a passageway, wherein no portion of the outer layer is in contact with the passageway, and thus no fluid is in contact with the outer layer, even at the face.

In one embodiment, the present disclosure provides a tube for use in a liquid chromatography or analytical instrument system, comprising an outer layer having an inner surface and an outer surface, and having a first and a second end, and a biocompatible inner layer having a passageway therethrough and having a first and a second end, wherein the inner layer is located within the outer layer. In certain embodiments, portions of the first and second ends of the biocompatible inner layer extend beyond the first and second ends, respectively, of the outer layer. In particular embodiments the outer layer is comprised of metal. In some embodiments the outer metal layer comprises stainless steel, and the biocompatible inner layer comprises a fluoropolymer or polyetheretherketone (PEEK).

The present disclosure further provides a tube for use in a liquid chromatography system, comprising an outer layer having an inner surface and an outer surface, and having a first and a second end, wherein the first and second ends of the outer metal layer are flanged, flared or angled, and a biocompatible inner layer having an inner surface, an outer surface, a first end, a second end and a passageway therethrough, wherein the inner layer is located within the outer layer. In certain embodiments the first and second ends of the biocompatible inner layer extend beyond the first and second ends, respectively, of the outer layer. In particular aspects the first and second ends of the inner layer are flanged, flared, or angled. In some embodiments the outer layer is comprised of metal, for example stainless steel. In various embodiments the biocompatible inner layer comprises a fluoropolymer or polyetheretherketone (PEEK).

In certain aspects of the present disclosure, at least a portion of the inner surface of the outer layer is attached to or interacts with at least a portion of the outer surface of the inner layer. In particular embodiments, at least 25%, at least 50%, at least 75%, at least 90%, or essentially the entire inner surface of the outer layer is attached to or interacts with the outer surface of the inner layer. In some embodiments the attachment or interaction between the outer layer and the inner layer is friction-based. In certain embodiments the attachment or interaction occurs through heating the tube, gluing the inner surface of the outer layer and the outer surface of the inner layer, crimping the outer layer onto the inner layer, or drawing the outer layer over the inner layer. Thus, in certain aspects of the present disclosure the inner layer and outer layer cannot rotate independently, while in other aspects the inner layer and the outer layer can rotate independently of each other.

In additional aspects of the present disclosure the tube further comprises at least a first fitting. In various embodiments the first fitting is a one-piece fitting or a two-piece fitting. In other embodiments the first fitting is removable. In further embodiments the tube further comprises at least a first and a second fitting.

The present disclosure further provides a tube for use in a liquid chromatography system, comprising an outer layer having an inner surface and an outer surface, and having a first and a second end, wherein at least one of the first and second ends of the outer layer comprises a tip portion and a retention feature, wherein the tip portion comprises a polymer, and a biocompatible inner layer having an inner surface, an outer surface, a first end, a second end and a passageway therethrough, wherein the inner layer is located within the outer layer. In certain embodiments the retention feature is a barb, an undercut, a groove, a thread, one or more cross-drilled hole, one or more dimple, a reverse taper, a flange, or a geometric shape, including, but not limited to, a square, a pentagon, a hexagon, a heptagon, or an octagon. In other embodiments the first end of the outer layer comprises a first tip portion and a first retention feature, and the second end of the outer layer comprises a second tip portion and a second retention feature, wherein the first and second tip portions comprise a polymer. In such embodiments the first retention feature can be the same as the second retention feature or the first retention feature can be different from the second retention feature.

In various embodiments the first and second ends of the biocompatible inner layer extend beyond the first and second ends, respectively, and the tip portion of the outer layer. In further embodiments the outer layer is comprised of metal, for example stainless steel. In additional embodiments the biocompatible inner layer comprises polyetheretherketone (PEEK). In other aspects tip portion comprises PEEK, for example carbon-fiber PEEK. In such embodiments the carbon fiber PEEK comprises about 10% to about 40% by weight carbon-fiber. In yet other embodiments the tip portion is molded onto at least one of the first and second ends of the outer layer.

In certain aspects the tube further comprises at least a first fitting assembly, while in other aspects the tube further comprises at least a first and a second fitting assembly. In various embodiments the fitting assembly comprises a nut having a first end and a second end, and having a passageway therethrough, wherein the passageway has an internally tapered portion and a lip proximal the second end of the nut, and wherein the second end of the nut has an externally threaded portion, a ferrule having a first externally tapered end and a second end and having a passageway therethrough, wherein the first externally tapered end of the ferrule is adapted to securely engage with the tapered portion of the passageway in the nut, and a ferrule tip having a first externally tapered end, a central portion, and a second externally tapered end, wherein the first externally tapered end and the central portion define a first lip and the second externally tapered end and the central portion define a second lip, and wherein the first end of the ferrule tip is adapted to abut with the second end of the ferrule within the passageway of the nut, and the first lip of the ferrule tip securely engages the lip of the nut. In particular embodiments the first externally tapered end of the ferrule comprises a plurality of members. In other embodiments the ferrule and the ferrule tip may rotate independently. In yet other embodiments the ferrule and the ferrule tip may actuate independently.

In certain embodiments at least a portion of an angle of the internally tapered portion of the nut and at least a portion of an angle of the first externally tapered end of the ferrule are between about 18° and about 28° included angle, and the angles of the portions of the internally tapered portion of the nut and the first externally tapered end of the ferrule differ by about 1° to about 5°. In further embodiments the nut, the ferrule, or the ferrule tip comprises a polymer, for example polyetheretherketone. In still further embodiments the polymer comprises about 10% to about 30% by weight carbon filled polyetheretherketone. In particular aspects the nut, the ferrule, or the ferrule tip comprises a metal, for example stainless steel. In some embodiments at least one of the nut, ferrule, and ferrule tip comprises polyetheretherketone and at least one of the nut, ferrule, and ferrule tip comprises stainless steel. In various embodiments the fitting assembly consists essentially of biocompatible materials.

In additional embodiments at least a portion of the passageway through the nut, the ferrule, or the ferrule tip is at least partially coated, while in other embodiments at least a portion of the passageway through the nut, the ferrule, and the ferrule tip is at least partially coated. In various embodiments at least a portion of the passageway through the nut, the ferrule, or the ferrule tip is at least partially coated with a coating comprising a nickel, silica carbide, copper or diamond coating, or a combination thereof.

The present disclosure additionally provides a tube and fitting system for use in a liquid chromatography system, comprising a tube comprising an outer layer having an inner surface and an outer surface, and having a first and a second end, wherein at least one of the first and second ends of the outer layer comprises a tip portion, wherein the tip portion comprises a polymer, and a biocompatible inner layer having a passageway therethrough and having a first and a second end, wherein the inner layer is located within the outer layer and a fitting comprising a first ferrule and a second ferrule, wherein the first ferrule comprises a metal, such as stainless steel, and the second ferrule comprises a polymer, wherein the first ferrule holds the tube by the outer layer and the second ferrule seals the tube on the tip portion.

The present disclosure further provides a tube assembly for use in a liquid chromatography system, comprising a tube comprising an outer layer having an inner surface and an outer surface, and having a first and a second end, wherein at least one of the first and second ends of the outer layer comprises a tip portion and a retention feature, wherein the tip portion comprises a polymer and a biocompatible inner layer having an inner surface, an outer surface, a first end, a second end and a passageway therethrough, wherein the inner layer is located within the outer layer, and at least a first fitting assembly associated with the first or second end of the outer layer. In certain aspects the retention feature is a barb, an undercut, a groove, a thread, one or more cross-drilled hole, one or more dimple, a reverse taper, a flange, or a geometric shape. In additional embodiments the first end of the outer layer comprises a first tip portion and a first retention feature, and the second end of the outer layer comprises a second tip portion and a second retention feature, wherein the first and second tip portions comprise a polymer. In such embodiments the first retention feature can be the same as the second retention feature, or the first retention can be different from the second retention feature.

In certain embodiments of the disclosed tube assembly, the fitting assembly comprises a nut having a first end and a second end, and having a passageway therethrough, wherein the passageway has an internally tapered portion and a lip proximal the second end of the nut, and wherein the second end of the nut has an externally threaded portion, a ferrule having a first externally tapered end and a second end and having a passageway therethrough, wherein the first externally tapered end of the ferrule is adapted to securely engage with the tapered portion of the passageway in the nut, and a ferrule tip having a first externally tapered end, a central portion, and a second externally tapered end, wherein the first externally tapered end and the central portion define a first lip and the second externally tapered end and the central portion define a second lip, and wherein the first end of the ferrule tip is adapted to abut with the second end of the ferrule within the passageway of the nut, and the first lip of the ferrule tip securely engages the lip of the nut.

The present disclosure also provides an analytical instrument system comprising at least one tube assembly comprising a tube comprising an outer layer having an inner surface and an outer surface, and having a first and a second end, wherein at least one of the first and second ends of the outer layer comprises a tip portion and a retention feature, wherein the tip portion comprises a polymer, and a biocompatible inner layer having an inner surface, an outer surface, a first end, a second end and a passageway therethrough, wherein the inner layer is located within the outer layer, and at least a first fitting assembly associated with the first or second end of the outer layer, the fitting assembly comprising a nut having a first end and a second end, and having a passageway therethrough, wherein the passageway has an internally tapered portion and a lip proximal the second end of the nut, and wherein the second end of the nut has an externally threaded portion, a ferrule having a first externally tapered end and a second end and having a passageway therethrough, wherein the first externally tapered end of the ferrule is adapted to securely engage with the tapered portion of the passageway in the nut, and a ferrule tip having a first externally tapered end, a central portion, and a second externally tapered end, wherein the first externally tapered end and the central portion define a first lip and the second externally tapered end and the central portion define a second lip, and wherein the first end of the ferrule tip is adapted to abut with the second end of the ferrule within the passageway of the nut, and the first lip of the ferrule tip securely engages the lip of the nut.

In certain embodiments the analytical instrument system comprises a liquid chromatography system. In such embodiments the analytical instrument system comprises an ultra high pressure or ultra high performance liquid chromatography system. In further embodiments the analytical instrument system comprises a high performance or high pressure liquid chromatography system, an ultra high performance or ultra high pressure liquid chromatography system, a mass spectrometry system, a microflow chromatography system, a nanoflow chromatography system, a nano-scale chromatography system, a capillary electrophoresis system, a reverse-phase gradient chromatography system, or a combination thereof.

The present disclosure additionally provides a process for preparing a tube for use in a liquid chromatography system, the tube comprising a biocompatible inner layer and an outer layer, the biocompatible inner layer and outer layer each comprising a first and a second end, and an inner surface and an outer surface, comprising treating the inner or outer layer to provide a tight fit between the inner and outer layers. In certain embodiments the process comprises cold drawing a biocompatible inner layer having a passageway therethrough and having a first and a second end, inserting the biocompatible inner layer into an outer layer having an inner surface and an outer surface, and having a first and a second end, and heating the inner and outer layers to provide a tight fit between the inner and outer layers.

These and other embodiments and advantages of the disclosed tube are described below.

BRIEF DESCRIPTION OF THE DRAWINGS

FIG. 6 is a side view of one embodiment of one end of a tube having a flanged, flared or angled end with a fitting assembly.

FIG. 7 is a cross-sectional side view of the embodiment of an end of a flanged, flared or angled tube with a fitting assembly as shown in FIG. 6.

FIG. 13 is a side view of one embodiment of a straight tube (without flanged ends) including a fitting assembly at each end in accordance with one aspect of the present invention.

FIG. 14 is a cross-sectional side view of one end of the tube and fitting assembly of FIG. 13.

DETAILED DESCRIPTION

Figure 1:
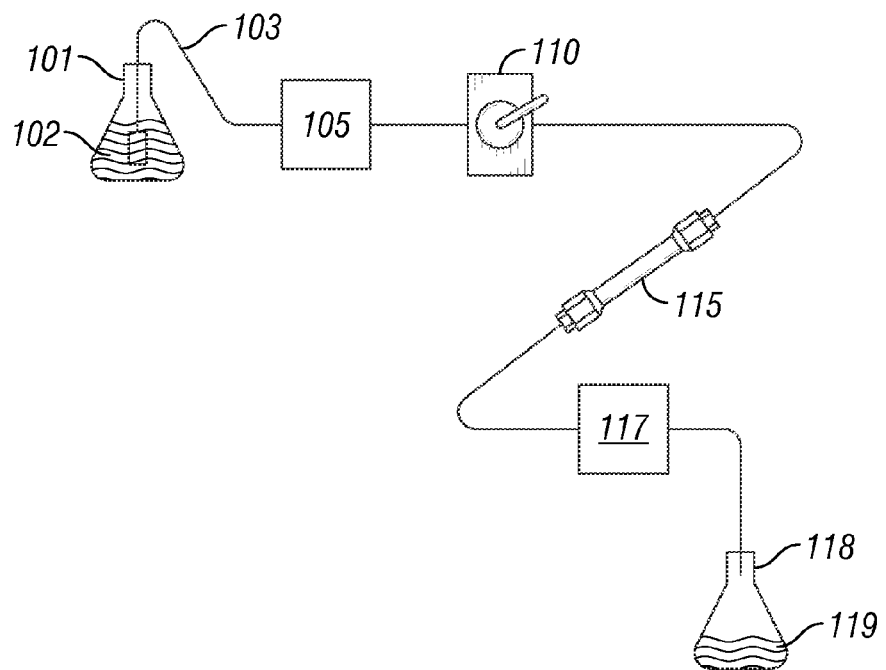
FIG. 1 is a block diagram of a conventional liquid chromatography system.

In FIG. 1, a block diagram of the essential elements of a conventional liquid chromatography (LC) system is provided. A reservoir 101 contains a solvent or mobile phase 102. Tubing 103 connects the mobile phase 102 in the reservoir 101 to a pump 105. The pump 105 is connected to a sample injection valve 110 which, in turn, is connected via tubing to a first end of a guard column (not shown). The second end of the guard column (not shown) is in turn connected to the first end of a primary column 115. The second end of the primary column 115 is then connected via tubing to a detector 117. After passing through the detector 117, the mobile phase 102 and the sample injected via injection valve 110 are expended into a second reservoir 118, which contains the chemical waste 119. As noted above, the sample injection valve 110 is used to inject a sample of a material to be studied into the LC system. The mobile phase 102 flows through the tubing 103 which is used to connect the various elements of the LC system together.

When the sample is injected via sample injection valve 110 in the LC system, the sample is carried by the mobile phase through the tubing into the column 115. As is well known in the art, the column 115 contains a packing material which acts to separate the constituent elements of the sample. After exiting the column 115, the sample (as separated via the column 115) then is carried to and enters a detector 117, which detects the presence or absence of various chemicals. The information obtained by the detector 117 can then be stored and used by an operator of the LC system to determine the constituent elements of the sample injected into the LC system. Those skilled in the art will appreciate that FIG. 1 and the foregoing discussion provide only a brief overview of a simplistic LC system that is conventional and well known in the art, as is shown and described in U.S. Pat. No. 5,472,598, issued Dec. 5, 1995 to Schick, which is hereby incorporated by reference as if fully set forth herein. Those skilled in the art will also appreciate that while the discussion herein focuses on a LC system, other analytical systems can be used in connection with various embodiments of the invention, such as a mass spectrometry, microflow chromatography, nanoflow chromatography, nano-scale liquid chromatography, capillary electrophoresis, or reverse-phase gradient chromatography system.

Preferably, for an LC system to be biocompatible, the various components (except where otherwise noted) that may come into contact with the effluent or sample to be analyzed are made of the synthetic polymer polyetheretherketone, which is commercially available under the trademark "PEEK" from Victrex. The polymer PEEK has the advantage of providing a high degree of chemical inertness and therefore biocompatibility; it is chemically inert to most of the common solvents used in LC applications, such as acetone, acetonitrile, and methanol (to name a few). PEEK also can be machined by standard machining techniques to provide smooth surfaces. Those skilled in the art will appreciate that other polymers may be desirable in certain applications.

Figure 2:
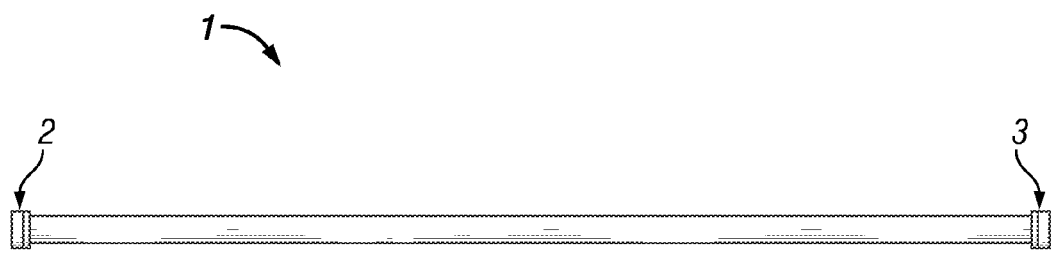
FIG. 2 is a side view of a tube with flanged, flared or angled ends in accordance with one aspect of the present invention.

Referring now to FIG. 2, a first embodiment of a tube 1 is shown. As shown in FIG. 2, the tube 1 includes a flanged first end 2 and a flanged second end 3.

Figure 3:
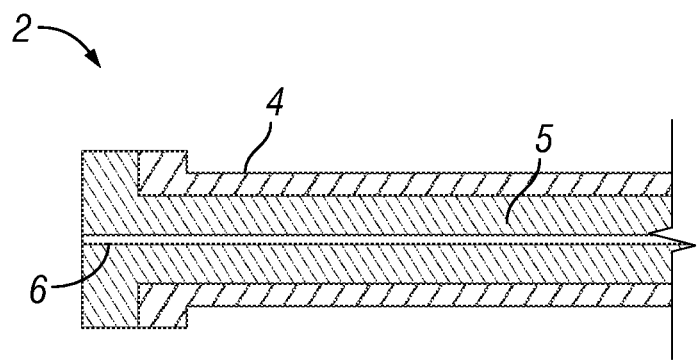
FIG. 3 is a cross-sectional side view of an end of an embodiment of the tube of FIG. 2 having flanged ends.

FIG. 3 shows a cross-section of one embodiment of a flanged first end 2 of the tube 1 as shown in FIG. 2. It can be seen that the flanged first end 2 of the tube 1 as shown has three distinct portions. These include an outer layer 4, an inner layer 5, and a passageway 6 defined by the inner layer 5. The inner layer 5 generally comprises a biocompatible material. The inner diameter of the inner layer 5 can be a variety of sizes, including, but not limited to 10 µm, 15 µm, 20 µm, 25 µm, 30 µm, 35 µm, 40 µm, 45 µm, 50 µm, 75 µm, 100 µm, 125 µm, 150 µm, 175 µm, 200 µm, 250 µm, or 500 µm, or so.

Figure 4:
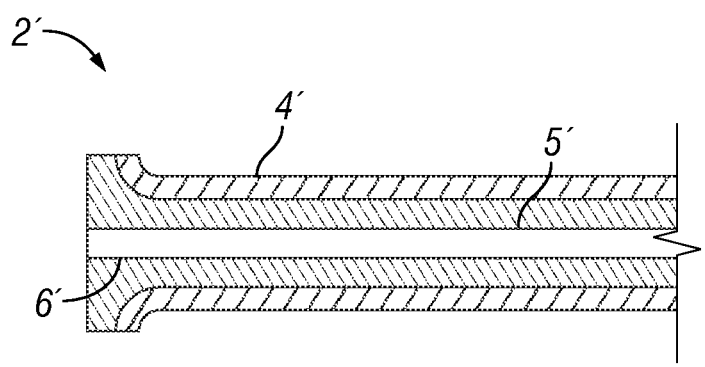
FIG. 4 is a cross-sectional side view of an end of an embodiment of the tube of FIG. 2 having flared ends.

FIG. 4 shows a cross-section of one embodiment of a flared first end 2' of the tube 1. It can be seen that the flared first end 2' of the tube 1 as shown also has three distinct portions. These include all outer layer 4', an inner layer 5', and a passageway 6' defined by the inner layer 5'. Once again, the inner layer 5' generally comprises a biocompatible material. The inner diameter of the inner layer 5' can be a variety of sizes, including, but not limited to 10 µm, 15 µm, 20 µm, 25 µm, 30 µm, 35 µm, 40 µm, 45 µm, 50 µm, 75 µm, 100 µm, 125 µm, 150 µm, 175 µm, 200 µm, 250 µm, or 500 µm, or so.

Figure 5:
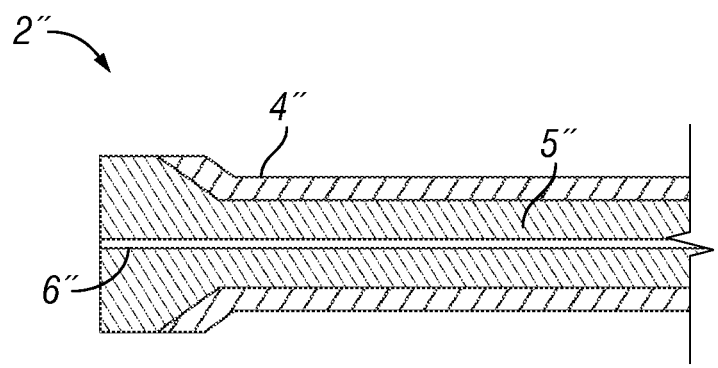
FIG. 5 is a cross-sectional side view of an end of a second embodiment of the tube of FIG. 2 having angled ends.

FIG. 5 shows a cross-section of one embodiment of an angled first end 2" of the tube 1. It can once again be seen that the angled first end 2" of the tube 1 as shown has three distinct portions. These include an outer layer 4", an inner layer 5", and a passageway 6" defined by the inner layer 5". Once again, the inner layer 5" generally comprises a biocompatible material. The inner diameter of the inner layer 5" can be a variety of sizes, including, but not limited to 10 µm, 15 µm, 20 µm, 25 µm, 30 µm, 35 µm, 40 µm, 45 µm, 50 µm, 75 µm, 100 µm, 125 µm, 150 µm, 175 µm, 200 µm, 250 µm, or 500 µm, or so.

It will be appreciated that the tube 1 can comprise a number of different materials depending on the particular application, as that may involve a particular type of sample, a particular type of solvent, and/or a particular pressure range. For example, the outer layer 4 (or 4' or 4") of tube 1 can comprise a metal, such as stainless steel (such as 316 stainless steel) or titanium, or a reinforced polymeric material, including composite or braided materials, such as polymeric materials that are reinforced or braided with carbon, carbon fibers, steel fibers, or the like. In embodiments comprising a metallic outer layer 4 (or 4' or 4"), the metal temper can be varied to provide a balance between high pressure capability and tubing flexibility. The inner layer 5 (or 5' or 5") can comprise a biocompatible polymer, such as polyetheretherketone (PEEK). Other polymer materials which may be used for the inner layer 5 (or 5' or 5") include, but are not limited to, TEFLON®, TEFZEL®, DELRIN®, perfluoroalkoxy (PFA, also called perfluoroalkoxyethylene), fluorinated ethylene propylene (PEP), polytetrafluoroethylene (PETE), ETFE (a polymer of tetrafluoroethylene and ethylene), polyetherimide (PEI), polyphenylene sulfide (PPS), polypropylene, sulfone polymers, polyolefins, polyimides, other polyaryletherketones, other fluoropolymers, polyoxymethylene (POM), and others, depending on the foregoing factors or perhaps others. In addition, PEEK (or other polymers) may be used that is reinforced or braided with carbon, carbon fibers, steel fibers, or the like. Furthermore, in certain embodiments the inner layer 5 (or 5' or 5") may be coated with a material to increase strength, improve chemical resistance, improve temperature stability, or reduce permeability. Such coatings include, but are not limited to, metallization, polymeric coating, silicon-based coatings, and carbon-based coatings. Additionally, in certain embodiments the inner layer may be heat treated to improve properties such as crystallinity, chemical resistance, or permeability. The final tube 1 may be treated to further improve the performance, including heat treatment or annealing to strengthen the polymer components, or pressurizing, with or without added heat, to allow the inner layer to conform to the outer layer. A mandrel can be used in the inner diameter of the inner layer to preserve the passageway.

Those skilled in the art will further appreciate that tube 1 as shown in FIG. 2 can comprise one or more fitting connection (not shown) for connecting tube 1 to another component in an LC, or other AI system (not shown), and that the other component may be any one of wide variety of components. Such components include pumps, columns, filters, guard columns, injection valves and other valves, detectors, pressure regulators, reservoirs, and other fittings, such as unions, tees, crosses, adapters, splitters, sample loops, connectors, and the like.

FIG. 6 shows an embodiment of one end of a flanged, flared or angled tube 1, as shown in FIG. 2, with an assembled fitting assembly 50 at the end of the tube 1. As detailed above, tube 1 comprises first end 2 and second end (not shown). Visible in the assembled fitting assembly 50 are first end 51, second end 53, nut head 52, first non-threaded portion 55, externally threaded portion 54, tapered portion 56, and second non-threaded portion 57. The passageway (not visible) is adapted to allow tube 1 to extend through the fitting assembly 50.

FIG. 7 shows a cross-section of the embodiment of one end of a flanged, flared or angled tube and assembled fitting assembly as shown in FIG. 6. It can be seen that the flanged first end 2 of the tube 1 as shown has three distinct portions. These include an outer layer 4, an inner layer 5, and a passageway 6 defined by the inner layer 5. The inner layer 5 generally comprises a biocompatible material. The inner diameter of the inner layer 5 can be a variety of sizes, including, but not limited to 10 µm, 15 µm, 20 µm, 25 µm, 30 µm, 35 µm, 40 µm, 45 µm, 50 µm, 75 µm, 100 µm, 125 µm, 150 µm, 175 µm, 200 µm, 250 µm, or 500 µm, or so. It can also be seen in FIG. 7 that fitting assembly 50 comprises first end 51, second end 53, nut head 52, first non-threaded portion 55, externally threaded portion 54, tapered portion 56, and second non-threaded portion 57. The passageway 58 (mostly obscured by tube 1) is adapted to allow tube 1 to extend through the fitting assembly 50.

Figure 8:
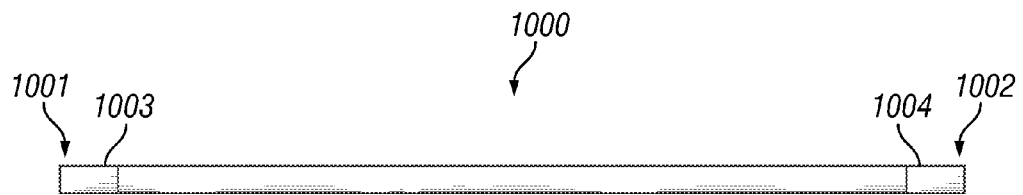
FIG. 8 is a side view of one embodiment of a straight tube (without flanged ends) in accordance with one aspect of the present invention.

Referring now to FIG. 8, an alternative embodiment of a tube 1000 is illustrated. Like the tube 1 of FIG. 2, the tube 1000 of FIG. 8 includes a first end 1001 and a second end 1002, but the first end 1001 and second end 1002 of tube 1000 are essentially straight instead of flanged, flared or angled. This allows any standard fitting assembly to be used with tube 1000.

In addition, tube 1000 includes a first tip assembly 1003 and a second tip assembly 1004. Those skilled in the art will appreciate that any fitting that can be used with an LC or other analytical instrument (AI) system can be used in conjunction with the tube 1000.

Figure 9:
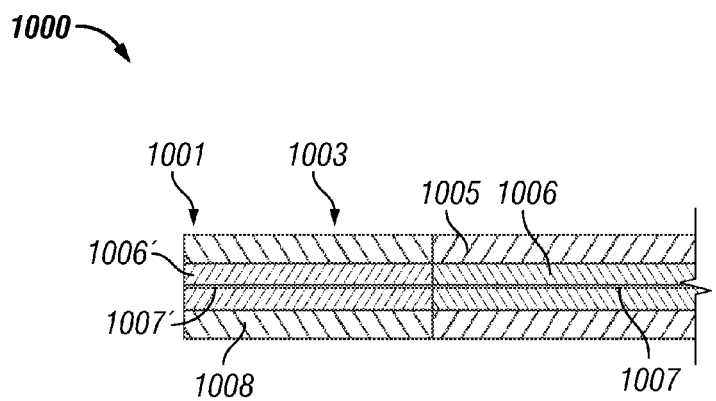
FIG. 9 is a cross-sectional side view of an end of an embodiment of the tube of FIG. 8.

FIG. 9 shows a cross-section of one embodiment of the first end 1001 and first tip assembly 1003 of the tube 1000 shown in FIG. 8. Tube 1000 again comprises three distinct portions, the outer layer 1005, the inner layer 1006, and a passageway 1007 defined by the inner layer 1006. The first tip assembly 1003 also comprises three distinct portions, an extension of the inner layer 1006' that protrudes from outer layer 1005, an extension of the passageway 1007' defined by the extension of the inner layer 1006', and a tip 1008 overmolded onto the extension of the inner layer 1006' and extension of the passageway 1007' that protrudes from outer layer 1005. One method of making tube 1000 is by extruding a precision polymer tube, and inserting it into a stainless steel tube. Coextruded polymer tubes can also be employed to tailor the material properties to the application. The ends of the polymer tube can be insert molded onto the tubing to provide an inert wetted face. For example, a PEEK liner tube can be used with a stainless steel tube including a carbon fiber reinforced tip. The tip to liner tube adhesion resulting from PEEK to PEEK insert molded bond prevents any liquid flowing between the layers. Carbon fiber tips can give the tubing added strength to resist damage from the fluid pressure and any compression from a fitting assembly.

Once again, it will be appreciated that the tube 1000 can comprise a number of different materials, depending on the particular application, as that may involve a particular type of sample, a particular type of solvent, and/or a particular pressure range. For example, the outer layer 1005 of tube 1000 can comprise a metal, such as stainless steel (such as 316 stainless steel) or titanium, while the inner layer 1006 can comprise a biocompatible polymer, such as polyetheretherketone (PEEK), fused silica, or coated fused silica, such as PEEK-coated fused silica. Other polymer materials which may be used for the inner layer 1006 include, but are not limited to, TEFLON®, TEFZEL®, DELRIN®, perfluoroalkoxy (PEA, also called perfluoroalkoxyethylene), fluorinated ethylene propylene (FEP), polytetrafluoroethylene (PETE), ETFE (a polymer of tetrafluoroethylene and ethylene), polyetherimide (PEI), polyphenylene sulfide (PPS), polypropylene, sulfone polymers, polyolefins, polyimides, other polyaryletherketones, other fluoropolymers, polyoxymethylene (POM), and others, depending on the foregoing factors or perhaps others. In addition, PEEK (or other polymers) may be used that is reinforced or braided with carbon, carbon fibers, glass fibers, steel fibers, or the like. In addition, steel tubes comprising unfilled PEEK tips can be used with unfilled PEEK liner tubing, and fluoropolymers (for example ethylene tetrafluoroethylene (TTE), fluorinated ethylene propylene (FEP), perfluoroalkoxy (PEA), polytetrafluoroethylene (PETE), polyvinylidenefluoride (PVDF) or modified fluoroalkoxy (MFA)) can be used in the tips and/or liner tubes. In addition, fluoropolymer tubing and tips and be used with a polymer (for example natural or braided PEEK) jacket for a totally nonmetallic version of tube 1000.

Furthermore, in certain embodiments the inner layer 1006 may be coated with a material to increase strength, improve chemical resistance, improve temperature stability, or reduce permeability. Such coatings include, but are not limited to, metallization, polymeric coating, silicon-based coatings, and carbon-based coatings. Additionally, in certain embodiments the inner layer may be heat treated to improve properties such as crystallinity, chemical resistance, or permeability. The final tube 1000 may be treated to further improve the performance, including heat treatment or annealing to strengthen the polymer components, or pressurizing, with or without added heat, to allow the inner layer to conform to the outer layer. A mandrel can be used in the inner diameter of the inner layer to preserve the passageway. Furthermore, the outer layer 1005 can be crimped to prevent or reduce the inner layer 1006 from sliding within the outer layer 1005.

Figure 10:
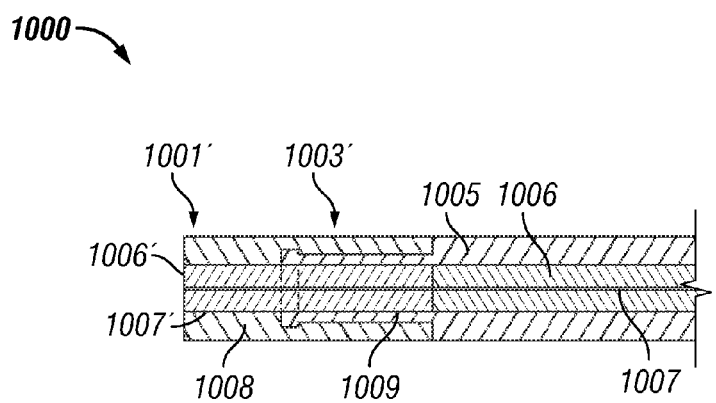
FIG. 10 is a cross-sectional side view of an end of another embodiment of the tube of FIG. 8.

FIG. 10 shows a cross-section of an alternative embodiment of the first end 1001' and first tip assembly 1003' of the tube 1000 shown in FIG. 8. Tube 1000 again comprises three distinct portions, the outer layer 1005, the inner layer 1006, and a passageway 1007 defined by the inner layer 1006. However, this embodiment of tube 1000 comprises a retention feature, which in this embodiment is a barb 1009, machined onto the end of the outer layer 1005, the inner layer 1006 protrudes from the barb 1009 of the outer layer 1005, and the barb 1009 and protruding portion 1006' of inner layer 1006 are overmolded together with tip 1008. One method of making tube 1000 is by extruding a precision polymer inner layer 1006, and inserting it into a stainless steel outer layer 1005 that comprises a barb 1009 at each end. Coextruded polymer tubes can also be employed to tailor the material properties to the application. Additionally, the surface of the inner layer 1006 can be modified to improve the bonding to the tip 1008, for example by surface roughening, plasma treatment, corona discharge, or other comparable method. The ends of the inner layer 1006' protrude beyond the outer layer 1005 to prevent or reduce occlusion of the inner diameter and allow the inner layer to be externally fixed so that it is well-centered within the tip during insert injection molding. The tip 1008 of the tube 1000 are insert injection molded onto the barb 1009 and protruding portion of inner layer 1006' and then trimmed to provide a one-piece construction with an all-polymer inert wetted face. Alternatively, the tip 1008 may be comprised of cut pieces of tubing that are welded over the barb 1009 and protruding portion of inner layer 1006' by RF welding or other bonding technique. While the embodiment of the tube 1000 in FIG. 10 includes a barb 1009 as the retention feature at the end of outer layer 1005, other geometries can be used as retention features to achieve similar results, such as undercuts, ribs, grooves, threads, one or more cross-drilled hole, one or more dimple, a reverse taper, a flange, a geometric shape, including, but not limited to, a triangle, a square, a rectangle, a pentagon, a hexagon, a heptagon, or an octagon, or surface roughening without a retention feature.

Figure 11:
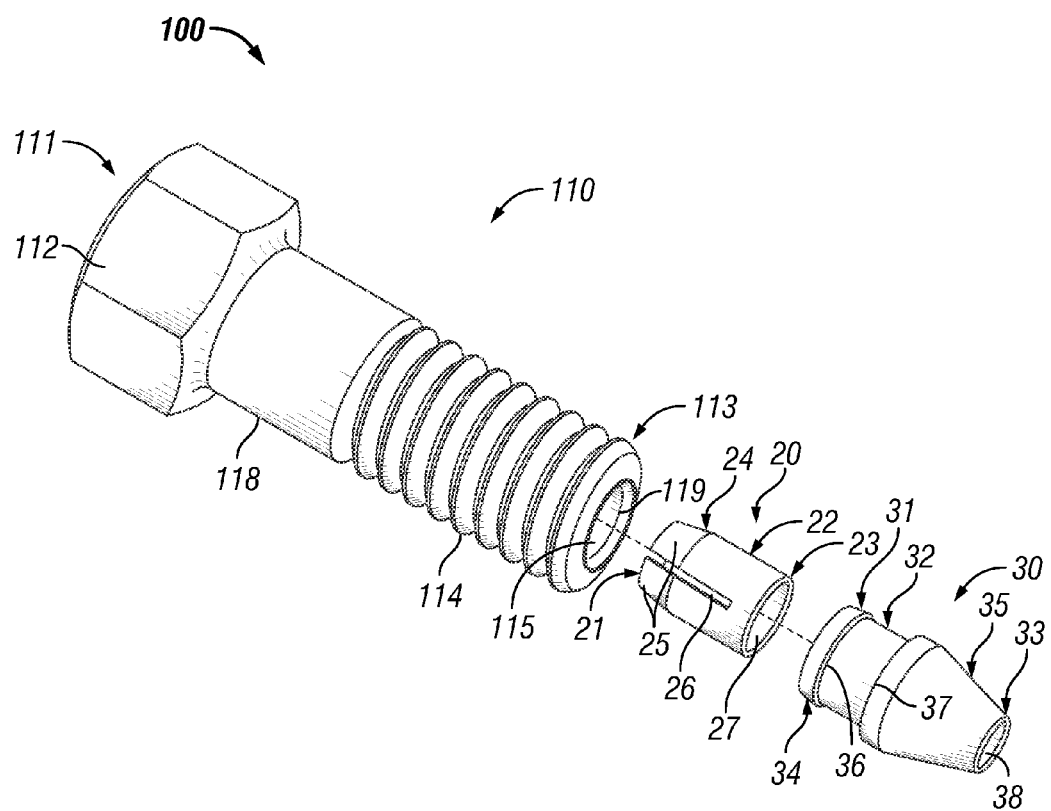
FIG. 11 is an exploded view of various components of an embodiment of a fitting assembly in accordance with one aspect of the present invention.

Referring now to FIG. 11, an embodiment of a fitting assembly 100 is shown. As shown in FIG. 11, the fitting assembly 100 includes a nut 110, a ferrule 20, and a ferrule tip 30. The first end 111 of the nut 110 includes a non-threaded portion 118 near the first end 111, and the nut head 112. The other or second end 113 of the nut 110 includes an externally threaded portion 114. Passageway 115 through nut 110 is also shown as is lip 119. As detailed below, passageway 115 and lip 119 are adapted to receive and securely hold a combination of the ferrule 20 and a first end of the ferrule tip 30. As shown in FIG. 11, each of nut 110, ferrule 20, and ferrule 30 are generally circular and symmetric about a center axis. Those skilled in the art will realize that a circular shape has advantages, but the outer diameters in particular of nut head 112 may have a non-circular shape if desired, such as having flat or concave surface portions, to allow an operator to more easily grip and rotate nut 110. As detailed herein, the externally threaded portion 114 of the nut 110 is adapted to be removably secured to a corresponding threaded portion of a port, a fitting, or a component of an LC or other analytical instrument (AI) system (not shown). Those skilled in the art will appreciate that the externally threaded portion 114 of the nut 110 may be adapted so that it can be removably engaged with any sized port, fitting, or component of an LC or other AI system (not shown). The use of external threads on one element, such as the nut 110, versus internal threads, is a matter of selection. Those skilled in the art will therefore appreciate that the nut 110 in an alternative embodiment could have internal threads (not shown) located near a second end, which could be engaged with external threads (not shown) located near the first end of an alternative embodiment of a port, fitting, or component of an LC or AI system (not shown).

Still referring to FIG. 11, it can be seen that the ferrule 20 as shown has three distinct portions. These include a first end 21, a middle portion 22, and a second end 23. First end 21 has a tapered portion 24 of the outer diameter so that the tapered portion 24 forms a truncated conical shape. As shown in FIG. 11, the tapered portion 24 of the first end 21 defines an angle from the axis of the ferrule 20. However, those skilled in the art will appreciate that the tapered portion 24 can define a different angle if desired. As detailed below, the tapered portion 24 of the first end 21 is adapted to be removably received in an internally tapered portion of passageway 115 of nut 110. Also shown is this embodiment of ferrule 20 are fingers or members 25, which define a slot 26 through the tapered portion 24 of the first end 21 and the middle portion 22 of the ferrule 20. Although only two fingers or members 25 are visible in FIG. 11, ferrule 20 can comprise a plurality of fingers or members, which in turn define a plurality of slots, which can extend any distance through the ferrule 20 from the first end portion 21 up to but not including the second end 23 of the ferrule 20. Passageway 27 through ferrule 20 is also shown.

Still referring to FIG. 11, it can be seen that the ferrule tip 30 as shown also has three distinct portions. Ferrule tip 30 includes a first end 31, a middle portion 32, and a second end 33. In this embodiment the first end 31 and second end 33 include first and second tapered portions 34 and 35, respectively, on the outer diameter of the ferrule tip 30 that are shaped as a truncated cone. First and second tapered portions 34 and 35 extend above the middle portion 32 of the ferrule tip 30, thereby forming first and second lips 36 and 37, respectively. As detailed below, the first end 31 of the ferrule tip 30 is adapted to abut the second end of ferrule 20 within the passageway 115 of the nut 110, and first lip 36 is adapted to be removably received in the passageway 115 of the nut 110. Passageway 38 through ferrule tip 30 is also shown. In general, we believe that the externally threaded portion 114 of the nut 110 and shape and size of the second tapered portion 35 of the ferrule tip 30 should be of a shape and size so that assembled fitting assembly 100 may be easily secured to a port, fitting, or component of a LC or AI system (not shown) and may also be easily removed there from, in either case by rotating the nut head 112 (and thereby fitting assembly 100) relative to the port, fitting, or component.

Generally, the rotational force or torque applied to connect to the nut 110, ferrule 20, ferrule tip 30 and tubing extending therethrough (not shown) to a port, fitting, or component in an LC or AI system accomplishes two major tasks. First, the force of the connection of the fitting assembly 100 needs to be sufficient to provide a sealed and leak proof connection to the port, fitting, or component. In addition, the force of the connection of the fitting assembly 100 needs to be sufficient so that the tubing is securely held and is sufficient to prevent detachment due to the hydraulic force of the fluid moving through the tubing. We believe that the latter function typically involves greater forces than the former. We believe that the fitting assembly 100 (such as shown in FIG. 11) provides an advantage in that it allows for better connections at higher pressures without requiring higher forces to connect fitting assembly 100.

Figure 12:
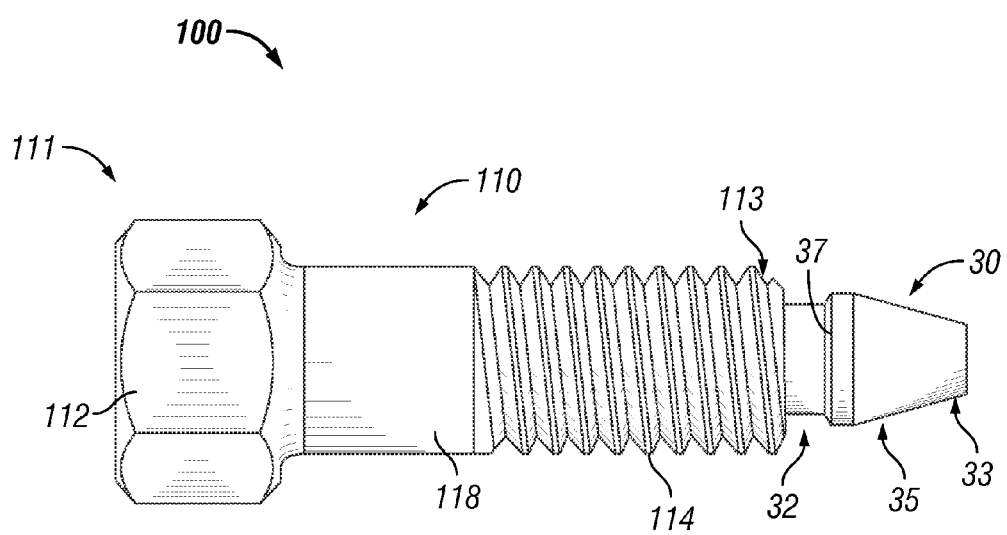
FIG. 12 is a side view of the fitting assembly of FIG. 11 when assembled.

FIG. 12 shows the embodiment of the fitting assembly 100 shown in FIG. 11 upon assembly by an operator. Like features and elements in the drawings have the same numerals in the various figures. Upon assembly of fitting assembly 100 only nut 110 and ferrule tip 30 are visible, as ferrule 20 (not visible) is positioned within the passageway 115 (not visible) of nut 110. Additionally, it can be seen that the first tapered portion 34 and first lip 36 of the first end 31 of the ferrule tip 30 are also not visible, as these elements are also positioned within the passageway 115 (not visible) of nut 110. Still visible upon assembly of the fitting assembly 100 are first end 111, second end 113, nut head 112, non-threaded portion 118, and externally threaded portion 114 of the nut 110, and middle portion 32, second end 33, second tapered portion 35, and second lip 37 of the ferrule tip 30. The passageways 115, 27, and 38 of the nut 110, ferrule 20, and ferrule tip 30 (not visible) are adapted to allow tubing (not shown) to extend through each of nut 110, ferrule 20, and fitting 30, and thus through the fitting assembly 100.

FIG. 13 shows an embodiment of a straight tube 1000, as shown in FIG. 8, with an assembled fitting assembly 100 as shown in FIG. 12 at each end of the tube 1000. As detailed above, tube 1000 comprises first end 1001 and second end 1002, and first tip assembly 1003 and second tip assembly 1004. Visible in each of the assembled fitting assemblies 100 are first end 111, second end 113, nut head 112, non-threaded portion 118, and externally threaded portion 114 of the nut 110, and middle portion 32, second end 33, second tapered portion 33, and second lip 37 of the ferrule tip 30. The passageways 115, 27, and 38 of the nut 110, ferrule 20, and ferrule tip 30 (not visible) are adapted to allow tube 1000 to extend through each of nut 110, ferrule 20, and fitting 30, and thus through the fitting assembly 100.

Additional details of the cross-section of the tube 1000 as shown in FIG. 8, the fitting assembly 100 as shown in FIG. 12, including the embodiment of the tip assembly as depicted in FIG. 10, are shown in FIG. 14. Nut 110 has a first end 111, a nut head 112, an unthreaded portion 118, a second end 113, and an externally threaded portion 114. Passageway 115 (largely excluded from view by tube 1000) extends through nut 110 and includes an internally tapered portion 116. The internally tapered portion 116 of the nut 110 is adapted to receive and securely hold the tapered portion 24 of the first end portion 21 of the ferrule 20 when the fitting assembly 100 is assembled. As shown in FIG. 14, the externally threaded portion 114 forms a lip 119 near the second end 113 of the nut 110. The externally threaded portion 114 of the nut 110 is adapted to be removably secured to a corresponding threaded portion of a port, a fitting, or a component of an LC or other analytical instrument (AI) system (not shown).

Additional details of the cross-section of the ferrule 20 are also shown in FIG. 14. The ferrule 20 has a first end 21 with an externally tapered portion 24, a middle portion 22 which in this embodiment, as shown in FIG. 14, is not tapered, and a second end 23. Although not shown, it will be appreciated that the angle of the tapered portion 24 from the axis of ferrule 20 may differ from the angle defined by the internally tapered portion 116 of the nut 110. For example, the angle defined by the tapered portion 24 of the ferrule 20 may be greater than the angle defined by the internally tapered portion 116 of the nut 110, to make it easier to obtain sufficient tubing retention with fitting assembly 100 when nut 110, ferrule 20, and ferrule tip 30 are engaged and assembled. As detailed above, the tapered portion 24 of the first end 21 of ferrule 20 is adapted to be removably received in the internally tapered portion 116 of passageway 115 of nut 110. Not shown in FIG. 14 are slots 26 extending through the tapered portion 24 of the first end 21 and the middle portion 22 of the ferrule 20. It will be appreciated by the skilled artisan that the slots 26 can extend any distance through the ferrule 20 from the first end portion 21 up to but not including the second end portion 23 of the ferrule 20. As shown in FIG. 12, the passageway 27 (not visible because occupied by tube 1000) through ferrule 20 is not tapered.

Additional details of the cross-section of the ferrule tip 30 are also shown in FIG. 14. The ferrule tip 30 has a first end 31, a middle portion 32, and a second end 33, and further has an externally tapered portion 34 at the first end 31 and an externally tapered portion 35 at the second end portion 33 of the ferrule lip 30. As shown in FIG. 14, the externally tapered portions 34 and 35 extend further from the central axis of the ferrule tip 30 than the middle portion 32, thereby defining a first lip 36 and a second lip 37, respectively, and the externally tapered portion 34 at the first end 31 of the ferrule tip 30 is tapered in the opposite direction compared to the externally tapered portion 35 at the second end 33 of the ferrule tip 30. The first end 31 of the ferrule 30 is adapted to abut the second end 23 of the ferrule 20 when the fitting assembly 100 is assembled. In addition, the first lip 36 is adapted to be securely retained by lip 119 in passageway 115 of the nut 110 when the fitting assembly 100 is assembled. Also shown in FIG. 14 is passageway 38 (not visible because occupied by tube 1000) extending through the ferrule tip 30.

FIG. 14 also shows a cross-section of an alternative embodiment of the first end 1001' and first tip assembly 1003' of the tube 1000 shown in FIG. 10. Tube 1000 again comprises three distinct portions, the outer layer 1005, the inner layer 1006, and a passageway 1007 defined by the inner layer 1006. However, this embodiment of tube 1000 comprises a barb 1009 machined onto the end of the outer layer 1005, a portion of the inner layer 1006' protrudes from the barb 1009 of the outer layer 1005, and the barb 1009 and protruding portion 1006' of inner layer 1006 are overmolded together with tip 1008.

Generally, the rotational force or torque applied to connect to the fitting assembly 100 and tube 1000 extending therethrough to a port, fitting, or component in an LC or AI system accomplishes two major tasks. First, the force of the connection of the fitting assembly 100 needs to be sufficient to provide a sealed and leak proof connection to the port, fitting, or component. In addition, the force of the connection of the fitting assembly 100 needs to be sufficient so that the tube 1000 is securely held and is sufficient to prevent detachment due to the hydraulic force of the fluid moving through the tube 1000.

It will be appreciated that the nut 110, ferrule 20, and ferrule tip 30 can comprise a number of different materials. For example, each of nut 110, ferrule 20 and ferrule tip 30 in a fitting assembly 100 can comprise a metal, such as stainless steel, or each can comprise a different material, such as a polymer. For example, the fitting assembly 100 can comprise a nut 110 comprising polyetheretherketone (PEEK), a ferrule 20 comprising stainless steel, and a ferrule tip 30 comprising PEEK. It will be appreciated that a variety of metals and polymers may be selected for any one or more of nut 110, ferrule 20, and ferrule tip 30 depending on the particular application, as that may involve a particular type of sample, a particular type of solvent, and/or a particular pressure range. In addition, the selection of materials for the tubing may lead to a selection of a particular material for nut 110, ferrule 20, and/or ferrule tip 30. In addition. PEEK (or other polymers) may be used that is reinforced with carbon, carbon fibers or steel fibers, or the like. Other polymer materials which may be used include, but are not limited to, TEFLON®, TEFZEL®, DELRIN®, polyphenylene sulfide (PPS), polypropylene, and others, depending on the foregoing factors or perhaps others. Those skilled in the art will further appreciate that fitting assembly 100 is shown as a fitting connection for connecting tubing to another component in an LC or other AI system, and that the other component may be any one of wide variety of components. Such components include pumps, columns, filters, guard columns, injection valves and other valves, detectors, pressure regulators, reservoirs, and other fittings, such as unions, tees, crosses, adapters, splitters, sample loops, connectors, and the like.

In order for a fitting assembly to seal, it should generally remain in compression (relative to the conical surface of the port) throughout all environmental conditions. Therefore, in certain aspects a coating with a high coefficient of friction between the outer surface of the tube material is applied to at least a portion of the internal bore surface of the described fitting assembly 100. The high coefficient of friction between the outer surface of the tube and the internal bore surface of the fitting connection or assembly 100 keeps the tube from extruding out of the port during pressurization, which results in dramatically increased burst pressure. In such embodiments the fitting connection or assembly is coated at the internal bore surface that contacts the tube starting at approximately 0.005 inches, about 0.0075 inches, about 0.01 inches, or about 0.02 inches from the tip. Coatings suitable for use with the presently described fitting connection or assembly include, but are not limited to, nickel, silica carbide, copper, and diamond coatings, and combinations thereof.

Methods of using the fitting assembly 100 (such as shown in FIG. 11 and FIG. 12) are now described in further detail. An operator can first provide a nut 110, ferrule 20 and ferrule tip 30, as well as tube 1000 (shown in FIG. 13 and FIG. 14). In one approach, the operator can insert a portion of the tube 1000 through the passageways 115, 27, and 38 of nut 110, ferrule 20 and ferrule tip 30, respectively, in that order without assembling or otherwise connecting any of nut 110, ferrule 20 and ferrule tip 30. Next, the operator can insert the ferrule 20 into the passageway 115 in the second end 113 of the nut 110, and the insert the first end 31 of the ferrule tip 30 into the passageway 115 in the nut 110, such that the first end 31 of the ferrule tip 30 abuts the second end 23 of the ferrule 20 and pushes the first end 21 of the ferrule 20 against the internal tapered portion 116 of the passageway 115 of the nut 110, and the first lip 34 of the ferrule tip 30 is retained within the passageway 115 of the nut 110 by lip 119. The operator can then engage the externally threaded portion 114 of the nut 110 with the internally threaded portion of a port, fitting, or component of a LC or AI system (not shown). Once the externally threaded portion 114 of the nut 110 and the internally threaded portion of the port, fitting, or component of a or AI system begin to mate or engage, the operator then rotates the nut head 112 of the fitting assembly 100 relative to the port, fitting, or component of a LC or AI system, rotates the port, fitting, or component of a LC or AI system relative to the nut head 112 of the fitting assembly 100, or rotates both the nut head 112 of the fitting assembly 100 and the port, fitting, or component of a LC or AI system relative to each other. By so rotating the nut head 112 of the fitting assembly 100 and the port, fitting, or component of a LC or AI system relative to one another, the operator drives the ferrule 20 and ferrule tip 30 further into the interior passageway 115 of the nut 110. In doing so, the operator thus forces the first end 21 of the ferrule 20 against the internally tapered portion 116 of the passageway 115 of nut 110 and also forces the externally tapered portion 34 of the first end of ferrule tip 30 into the passageway 115 of the nut 110, thus engaging the first lip 36 of the ferrule tip 30 with the lip 119 of the passageway 115 of the nut 110. In doing so, the externally tapered first end 24 of the ferrule 20 is compressed and held firmly against the internally tapered portion 116 of the passageway 115 of the nut 110, thereby forming a leak proof connection. Because the first ends 24 of the ferrule 20 may be deformed or compressed as it is forced against the tapered portion 116 of the passageway 115 of the nut 110, a leak proof connection may be obtained by the operator without the use of additional tools such as a wrench, pliers or the like. Alternatively, fitting assembly 100 can be provided to the operator pre-assembled. In one specific embodiment, when tubing having an outer diameter of 0.0625 inches is used, the minimum diameter of the passageway in the fitting assembly can range between about 0.065 and about 0.067 inches.

To disconnect a fitting assembly 100, such as shown in FIG. 11 and FIG. 12, an operator may either rotate the fitting assembly 100 relative to the port, fitting, or component of a LC or AI system (not shown), rotate the port, fitting, or component of a LC or AI system relative to the fitting assembly 100, or rotate both the port, fitting, or component of a LC or AI system and the fitting assembly 100 relative to each other. By rotating the port, fitting, or component of a LC or AI system and/or the fitting assembly 100 relative to one another, the operator thus rotates the externally threaded portion 114 of nut 110 and the internally threaded portion of the port, fitting, or component of a LC or AI system, respectively, and thereby disengages the connection between such threaded portions. At this point, the operator can use the assembly 100 and the leak proof connection it provides, until the operator decides to remove the tube 1000 (shown in FIG. 13 and FIG. 14) from the assembly 100. By selecting the direction of the threading of the externally threaded portion 114 of the nut 110 and internally threaded portion of the port, fitting, or component of a LC or AI system, respectively, the operator can turn the entire fitting assembly 100 (when connected) by turning or rotating nut 110, such that the fitting assembly 100 rotates relative to the port, fitting, or component of a LC or AI system (not shown) and disengages therefrom. Thus, the entire fitting assembly 100 is easily disconnected from the port, fitting, or component of a LC or AI system (not shown).

The following example is included to demonstrate preferred embodiments of the invention. It should be appreciated by those of skill in the art that the techniques disclosed in the example which follows represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein, will become apparent to those skilled in the art from the foregoing description. Such modifications are intended to fall within the scope of the appended claims.

Performance of a flanged tube 1 as described herein, for example as shown in FIG. 2, and straight tube 1000 as described herein, for example as shown in FIG. 6, were tested as detailed below. In a first test, it was determined that flanged tube 1 held to over 30,000 psi at about 4.0 inch-pounds of torque, prior to failure of the tube. In the second test, it was determined that straight tube 1000 held to about 30,000 psi at about 10.0 inch-pounds of torque, prior to failure of the fitting system. The design is such that a fitting can apply direct pressure to the flange face seal, allowing a high pressure seal with low actuation torque.

While the present invention has been shown and described in various embodiments, those skilled in the art will appreciate from the drawings and the foregoing discussion that various changes, modifications, and variations may be made without departing front the spirit and scope of the invention as set forth in the claims. Hence the embodiments shown and described in the drawings and the above discussion are merely illustrative and do not limit the scope of the invention as defined in the claims herein. The embodiments and specific forms, materials, and the like are merely illustrative and do not limit the scope of the invention or the claims herein.

We claim:

1. A tube for use in a liquid chromatography system, comprising:
    a) an outer layer having an inner surface and an outer surface, and having a first and a second end, wherein at least one of said first and second ends of said outer layer comprises a tip portion and a retention feature for retaining said tip portion, wherein said tip portion comprises a polymer and wherein said retention feature is a barb, an undercut, one or more cross-drilled hole, a reverse taper or a flange; and
    b) a biocompatible inner layer having an inner surface, an outer surface, a first end, a second end and a passageway therethrough, wherein said inner layer is located within said outer layer.

2. The tube according to claim 1, wherein said first end of said outer layer comprises a first tip portion and a first retention feature, and said second end of said outer layer comprises a second tip portion and a second retention feature, wherein said first and second tip portions comprise a polymer.

3. The tube according to claim 1, wherein said outer layer is comprised of metal.

4. The tube according to claim 1, wherein said biocompatible inner layer comprises polyetheretherketone (PEEK).

5. The tube according to claim 1, wherein at least a portion of said inner surface of said outer layer interacts with at least a portion of said outer surface of said inner layer.

6. The tube according to claim 5, wherein said interaction is friction-based.

7. The tube according to claim 1, wherein said tip portion comprises PEEK.

8. The tube according to claim 1, further comprising at least a first fitting assembly.

9. The tube according to claim 8, further comprising at least a first and a second fitting assembly.

10. The tube according to claim 8, wherein said fitting assembly comprises:
    a) a nut having a first end and a second end, and having a passageway therethrough, wherein said passageway has an internally tapered portion and a lip proximal said second end of said nut, and wherein said second end of said nut has an externally threaded portion;
    b) a ferrule having a first externally tapered end and a second end and having a passageway therethrough, wherein said first externally tapered end of said ferrule is adapted to securely engage with said tapered portion of said passageway in said nut; and
    c) a ferrule tip having a first externally tapered end, a central portion, and a second externally tapered end, wherein said first externally tapered end and said central portion define a first lip and said second externally tapered end and said central portion define a second lip, and wherein said first end of said ferrule tip is adapted to abut with said second end of said ferrule within said passageway of said nut, and said first lip of said ferrule tip securely engages said lip of said nut.

11. A tube assembly for use in a liquid chromatography system, comprising:
    a) a tube comprising:
        i) an outer layer having an inner surface and an outer surface, and having a first and a second end, wherein at least one of said first and second ends of said outer layer comprises a tip portion and a retention feature for retaining said tip portion, wherein said tip portion comprises a polymer and wherein said retention feature is a barb, an undercut, one or more cross-drilled hole, a reverse taper or a flange; and
        ii) a biocompatible inner layer having an inner surface, an outer surface, a first end, a second end and a passageway therethrough, wherein said inner layer is located within said outer layer; and
    b) at least a first fitting assembly associated with said first or second end of said outer layer.

12. The tube assembly according to claim 11, wherein said first end of said outer layer comprises a first tip portion and a first retention feature, and said second end of said outer layer comprises a second tip portion and a second retention feature, wherein said first and second tip portions comprise a polymer.

13. The tube assembly of claim 12, wherein said first retention feature is the same as said second retention feature.

14. An analytical instrument system comprising at least one tube assembly comprising:
    a) a tube comprising:
        i) an outer layer having an inner surface and an outer surface, and having a first and a second end, wherein at least one of said first and second ends of said outer layer comprises a tip portion and a retention feature for retaining said tip portion, wherein said tip portion comprises a polymer and wherein said retention feature is a barb, an undercut, one or more cross-drilled hole, a reverse taper or a flange; and
  ii) a biocompatible inner layer having an inner surface, an outer surface, a first end, a second end and a passageway therethrough, wherein said inner layer is located within said outer layer; and
b) at least a first fitting assembly associated with said first or second end of said outer layer, said fitting assembly comprising:
  i) a nut having a first end and a second end, and having a passageway therethrough, wherein said passageway has an internally tapered portion and a lip proximal said second end of said nut, and wherein said second end of said nut has an externally threaded portion;
  ii) a ferrule having a first externally tapered end and a second end and having a passageway therethrough, wherein said first externally tapered end of said ferrule is adapted to securely engage with said tapered portion of said passageway in said nut; and
  iii) a ferrule tip having a first externally tapered end, a central portion, and a second externally tapered end, wherein said first externally tapered end and said central portion define a first lip and said second externally tapered end and said central portion define a second lip, and wherein said first end of said ferrule tip is adapted to abut with said second end of said ferrule within said passageway of said nut, and said first lip of said ferrule tip securely engages said lip of said nut.

15. The system according to claim 14, wherein said analytical instrument system comprises an ultra high pressure or ultra high performance liquid chromatography system.

* * * * *